United States Patent
Carlton (10) Patent No.: US 7,951,149 B2
(45) Date of Patent: May 31, 2011

(54) ABLATIVE MATERIAL FOR USE WITH TISSUE TREATMENT DEVICE

(75) Inventor: John D. Carlton, Las Vegas, NV (US)

(73) Assignee: TYCO Healthcare Group LP, Boulder, CO (US)

( * ) Notice: Subject to any disclaimer, the term of this patent is extended or adjusted under 35 U.S.C. 154(b) by 874 days.

(21) Appl. No.: 11/581,850

(22) Filed: Oct. 17, 2006

(65) Prior Publication Data

US 2008/0091189 A1    Apr. 17, 2008

(51) Int. Cl.
*A61B 18/14* (2006.01)
(52) U.S. Cl. .............................. 606/51; 606/38; 606/52
(58) Field of Classification Search ............... 606/50–52
See application file for complete search history.

(56) References Cited

U.S. PATENT DOCUMENTS

| | | | |
|---|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,305,156 A | 4/1941 | Grubel |
| 2,279,753 A | 4/1942 | Knopp |
| 2,632,661 A | 8/1948 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,720,896 A | 3/1973 | Beierlein |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |

(Continued)

FOREIGN PATENT DOCUMENTS

CA    2104423    2/1994

(Continued)

OTHER PUBLICATIONS

Sigel et al. "The Mechanism of Blood Vessel Closure by High Frequency Electrocoagulation" Surgery Gynecology & Obstetrics, Oct. 1965 pp. 823-831.

(Continued)

*Primary Examiner* — Lee S Cohen
*Assistant Examiner* — Samantha Good (57) ABSTRACT

An electrosurgical instrument for treating tissue includes a housing having at least one tissue treating member attached thereto. The tissue treating member includes an electrically conductive tissue contacting surface connected to a source of electrosurgical energy such that the tissue contacting surface is capable of conducting electrosurgical energy to tissue. An energy conductive, ablative material is disposed on the electrically conductive tissue contacting surface and is configured to at least partially deplete during electrosurgical activation to reduce tissue adhesion.

12 Claims, 4 Drawing Sheets

U.S. PATENT DOCUMENTS

| | | | |
|---|---|---|---|
| 4,005,714 A | 2/1977 | Hiltebrandt | |
| 4,041,952 A | 8/1977 | Morrison, Jr. et al. | |
| 4,043,342 A | 8/1977 | Morrison, Jr. | |
| 4,074,718 A | 2/1978 | Morrison, Jr. | |
| 4,088,134 A | 5/1978 | Mazzariello | |
| 4,112,950 A | 9/1978 | Pike | |
| 4,127,222 A | 11/1978 | Adams | |
| 4,128,099 A | 12/1978 | Bauer | |
| 4,165,746 A | 8/1979 | Burgin | |
| 4,233,734 A | 11/1980 | Bies | |
| 4,300,564 A | 11/1981 | Furihata | |
| D263,020 S | 2/1982 | Rau, III | |
| 4,370,980 A | 2/1983 | Lottick | |
| 4,375,218 A | 3/1983 | DiGeronimo | |
| 4,416,276 A | 11/1983 | Newton et al. | |
| 4,418,692 A | 12/1983 | Guay | |
| 4,452,246 A | 6/1984 | Bader et al. | |
| 4,492,231 A | 1/1985 | Auth | |
| 4,552,143 A | 11/1985 | Lottick | |
| 4,574,804 A | 3/1986 | Kurwa | |
| 4,597,379 A | 7/1986 | Kihn et al. | |
| 4,600,007 A | 7/1986 | Lahodny et al. | |
| 4,655,215 A | 4/1987 | Pike | |
| 4,655,216 A | 4/1987 | Tischer | |
| 4,657,016 A | 4/1987 | Garito et al. | |
| 4,662,372 A | 5/1987 | Sharkany et al. | |
| 4,671,274 A | 6/1987 | Sorochenko | |
| 4,685,459 A | 8/1987 | Xoch et al. | |
| D295,893 S | 5/1988 | Sharkany et al. | |
| D295,894 S | 5/1988 | Sharkany et al. | |
| 4,754,892 A | 7/1988 | Retief | |
| 4,763,669 A | 8/1988 | Jaeger | |
| 4,827,929 A | 5/1989 | Hodge | |
| 4,846,171 A | 7/1989 | Kauphusman et al. | |
| 4,887,612 A | 12/1989 | Esser et al. | |
| 4,938,761 A | 7/1990 | Ensslin | |
| 4,985,030 A | 1/1991 | Melzer et al. | |
| 5,007,908 A | 4/1991 | Rydell | |
| 5,026,370 A | 6/1991 | Lottick | |
| 5,035,695 A | 7/1991 | Weber, Jr. et al. | |
| 5,084,057 A | 1/1992 | Green et al. | |
| 5,099,840 A | 3/1992 | Goble et al. | |
| 5,116,332 A | 5/1992 | Lottick | |
| 5,147,357 A | 9/1992 | Rose et al. | |
| 5,151,102 A | 9/1992 | Xamiyama et al. | |
| 5,176,695 A | 1/1993 | Dulebohn | |
| 5,190,541 A | 3/1993 | Abele et al. | |
| 5,196,009 A | 3/1993 | Kirwan, Jr. | |
| 5,197,964 A | 3/1993 | Parins | |
| 5,215,101 A | 6/1993 | Jacobs et al. | |
| 5,217,457 A | 6/1993 | Delahuerga et al. | |
| 5,217,458 A | 6/1993 | Parins | |
| 5,217,460 A | 6/1993 | Knoepfler | |
| 5,219,354 A | 6/1993 | Choudhury et al. | |
| 5,244,462 A | 9/1993 | Delahuerga et al. | |
| 5,250,047 A | 10/1993 | Rydell | |
| 5,250,063 A | 10/1993 | Abidin et al. | |
| 5,258,001 A | 11/1993 | Corman | |
| 5,258,006 A | 11/1993 | Rydell et al. | |
| 5,261,918 A | 11/1993 | Phillips et al. | |
| 5,275,615 A | 1/1994 | Rose | |
| 5,277,201 A | 1/1994 | Stern | |
| 5,282,799 A | 2/1994 | Rydell | |
| 5,290,286 A | 3/1994 | Parins | |
| 5,304,203 A | 4/1994 | El-Mallawany et al. | |
| 5,308,357 A | 5/1994 | Lichtman | |
| 5,314,445 A | 5/1994 | Degwitz et al. | |
| 5,318,589 A | 6/1994 | Lichtman | |
| 5,324,289 A | 6/1994 | Eggers | |
| 5,326,806 A | 7/1994 | Yokoshima et al. | |
| 5,330,471 A | 7/1994 | Eggers | |
| 5,334,183 A | 8/1994 | Wuchinich | |
| 5,334,215 A | 8/1994 | Chen | |
| 5,336,220 A | 8/1994 | Ryan et al. | |
| 5,336,221 A | 8/1994 | Anderson | |
| 5,342,359 A | 8/1994 | Rydell | |
| 5,342,381 A | 8/1994 | Tidemand | |
| 5,342,393 A | 8/1994 | Stack | |
| 5,344,424 A | 9/1994 | Roberts et al. | |
| 5,352,222 A | 10/1994 | Rydell | |
| 5,354,271 A | 10/1994 | Voda | |
| 5,356,408 A | 10/1994 | Rydell | |
| 5,366,477 A | 11/1994 | LeMarie, III et al. | |
| 5,368,600 A | 11/1994 | Failla et al. | |
| 5,376,089 A | 12/1994 | Smith | |
| 5,383,897 A | 1/1995 | Wholey | |
| 5,389,098 A | 2/1995 | Tsuruta et al. | |
| 5,389,104 A | 2/1995 | Hahnen et al. | |
| 5,391,166 A | 2/1995 | Eggers | |
| 5,391,183 A | 2/1995 | Janzen et al. | |
| 5,396,900 A | 3/1995 | Slater et al. | |
| 5,403,312 A | 4/1995 | Yates et al. | |
| 5,411,519 A | 5/1995 | Tovey et al. | |
| 5,411,520 A | 5/1995 | Nash et al. | |
| 5,413,571 A | 5/1995 | Katsaros et al. | |
| 5,415,657 A | 5/1995 | Taymor-Luria | |
| 5,422,567 A | 6/1995 | Matsunaga | |
| 5,423,810 A | 6/1995 | Goble et al. | |
| 5,425,690 A | 6/1995 | Chang | |
| 5,425,739 A | 6/1995 | Jessen | |
| 5,429,616 A | 7/1995 | Schaffer | |
| 5,431,672 A | 7/1995 | Cote et al. | |
| 5,431,674 A | 7/1995 | Basile et al. | |
| 5,437,292 A | 8/1995 | Kipshidze et al. | |
| 5,438,302 A | 8/1995 | Goble | |
| 5,441,517 A | 8/1995 | Kensey et al. | |
| 5,443,463 A | 8/1995 | Stern et al. | |
| 5,443,464 A | 8/1995 | Russell et al. | |
| 5,443,480 A | 8/1995 | Jacobs et al. | |
| 5,445,638 A | 8/1995 | Rydell et al. | |
| 5,445,658 A | 8/1995 | Durrfeld et al. | |
| 5,451,224 A | 9/1995 | Goble et al. | |
| 5,456,684 A | 10/1995 | Schmidt et al. | |
| 5,458,598 A | 10/1995 | Feinberg et al. | |
| 5,460,629 A | 10/1995 | Shlain et al. | |
| 5,462,546 A | 10/1995 | Rydell | |
| 5,472,443 A | 12/1995 | Cordis et al. | |
| 5,478,351 A | 12/1995 | Meade et al. | |
| 5,480,409 A | 1/1996 | Riza | |
| 5,484,436 A | 1/1996 | Eggers et al. | |
| 5,496,312 A | 3/1996 | Klicek | |
| 5,496,317 A | 3/1996 | Goble et al. | |
| 5,496,347 A | 3/1996 | Hashiguchi et al. | |
| 5,499,997 A | 3/1996 | Sharpe et al. | |
| 5,509,922 A | 4/1996 | Aranyi et al. | |
| 5,514,134 A | 5/1996 | Rydell et al. | |
| 5,527,313 A | 6/1996 | Scott et al. | |
| 5,531,744 A | 7/1996 | Nardella et al. | |
| 5,536,251 A | 7/1996 | Evard et al. | |
| 5,540,684 A | 7/1996 | Hassler, Jr. | |
| 5,540,685 A | 7/1996 | Parins et al. | |
| 5,540,715 A | 7/1996 | Katsaros et al. | |
| 5,542,945 A | 8/1996 | Fritzsch | |
| 5,549,604 A * | 8/1996 | Sutcu et al. | 606/45 |
| 5,558,671 A | 9/1996 | Yates | |
| 5,558,672 A | 9/1996 | Edwards et al. | |
| 5,562,699 A | 10/1996 | Heimberger et al. | |
| 5,569,241 A | 10/1996 | Edwardds | |
| 5,569,243 A | 10/1996 | Kortenbach et al. | |
| 5,571,100 A | 11/1996 | Goble et al. | |
| 5,573,424 A | 11/1996 | Poppe | |
| 5,573,534 A | 11/1996 | Stone | |
| 5,573,535 A | 11/1996 | Viklund | |
| 5,575,805 A | 11/1996 | Li | |
| 5,578,052 A | 11/1996 | Koros et al. | |
| 5,582,611 A | 12/1996 | Tsuruta et al. | |
| 5,585,896 A | 12/1996 | Yamazaki et al. | |
| 5,590,570 A | 1/1997 | LeMaire, III et al. | |
| 5,601,601 A | 2/1997 | Tal et al. | |
| 5,603,711 A | 2/1997 | Parins et al. | |
| 5,603,723 A | 2/1997 | Aranyi et al. | |
| 5,611,798 A | 3/1997 | Eggers | |
| 5,620,453 A | 4/1997 | Nallakrishnan | |
| 5,624,452 A | 4/1997 | Yates | |
| 5,626,578 A | 5/1997 | Tihon | |
| 5,626,609 A | 5/1997 | Zvenyatsky et al. | |
| 5,630,833 A | 5/1997 | Katsaros et al. | |

| | | | | | |
|---|---|---|---|---|---|
| 5,637,110 A | 6/1997 | Pennybacker et al. | 5,951,549 A | 9/1999 | Richardson et al. |
| 5,638,003 A | 6/1997 | Hall | 5,954,720 A | 9/1999 | Wilson et al. |
| 5,643,294 A | 7/1997 | Tovey et al. | 5,957,923 A | 9/1999 | Hahnen et al. |
| 5,647,869 A | 7/1997 | Goble et al. | 5,960,544 A | 10/1999 | Beyers |
| 5,647,871 A | 7/1997 | Levine et al. | 5,961,514 A | 10/1999 | Long et al. |
| 5,649,959 A | 7/1997 | Hannam et al. | 5,964,758 A | 10/1999 | Dresden |
| 5,658,281 A | 8/1997 | Heard | 5,976,132 A | 11/1999 | Morris |
| 5,662,667 A | 9/1997 | Knodel | 5,984,939 A | 11/1999 | Yoon |
| 5,665,100 A | 9/1997 | Yoon | 5,989,277 A | 11/1999 | LeMaire, III et al. |
| 5,667,526 A | 9/1997 | Levin | 5,997,565 A | 12/1999 | Inoue |
| 5,674,220 A | 10/1997 | Fox et al. | 6,004,335 A | 12/1999 | Vaitekunas et al. |
| 5,681,282 A | 10/1997 | Eggers et al. | 6,010,516 A | 1/2000 | Hulka et al. |
| 5,688,270 A | 11/1997 | Yates et al. | 6,024,741 A | 2/2000 | Williamson et al. |
| 5,693,051 A | 12/1997 | Schulze et al. | 6,024,744 A | 2/2000 | Kese et al. |
| 5,695,522 A | 12/1997 | LeMaire, III et al. | 6,030,384 A | 2/2000 | Nezhat |
| 5,700,261 A | 12/1997 | Brinkerhoff | 6,033,399 A | 3/2000 | Gines |
| 5,702,390 A | 12/1997 | Austin et al. | 6,039,733 A | 3/2000 | Buysse et al. |
| 5,707,369 A | 1/1998 | Vaitekunas et al. | 6,041,679 A | 3/2000 | Slater et al. |
| 5,709,680 A | 1/1998 | Yates et al. | 6,050,996 A | 4/2000 | Schmaltz et al. |
| 5,716,366 A | 2/1998 | Yates | 6,053,914 A | 4/2000 | Eggers et al. |
| 5,720,744 A | 2/1998 | Eggleston et al. | 6,053,933 A | 4/2000 | Balazs et al. |
| 5,722,421 A | 3/1998 | Francese et al. | D424,694 S | 5/2000 | Tetzlaff et al. |
| 5,725,536 A | 3/1998 | Oberlin et al. | D425,201 S | 5/2000 | Tetzlaff et al. |
| 5,727,428 A | 3/1998 | LeMaire, III et al. | 6,059,782 A | 5/2000 | Novak et al. |
| 5,735,848 A | 4/1998 | Yates et al. | 6,074,386 A | 6/2000 | Goble et al. |
| 5,743,906 A | 4/1998 | Parins et al. | RE36,795 E | 7/2000 | Rydell |
| 5,755,717 A | 5/1998 | Yates et al. | 6,083,223 A | 7/2000 | Baker |
| 5,766,130 A | 6/1998 | Selmonosky | 6,086,586 A | 7/2000 | Hooven |
| 5,766,166 A | 6/1998 | Hooven | 6,090,107 A | 7/2000 | Borgmeier et al. |
| 5,766,170 A | 6/1998 | Eggers | 6,096,037 A | 8/2000 | Mulier et al. |
| 5,769,849 A | 6/1998 | Eggers | 6,099,550 A | 8/2000 | Yoon |
| 5,772,655 A | 6/1998 | Bauer et al. | 6,102,909 A | 8/2000 | Chen et al. |
| 5,772,670 A | 6/1998 | Brosa | 6,110,171 A | 8/2000 | Rydell |
| 5,776,128 A | 7/1998 | Eggers | 6,113,596 A | 9/2000 | Hooven et al. |
| 5,776,130 A | 7/1998 | Buysse et al. | 6,113,598 A | 9/2000 | Baker |
| 5,779,701 A | 7/1998 | McBrayer et al. | 6,117,158 A | 9/2000 | Measamer et al. |
| H1745 H | 8/1998 | Paraschac | 6,123,701 A | 9/2000 | Nezhat |
| 5,792,137 A | 8/1998 | Carr et al. | H1904 H | 10/2000 | Yates et al. |
| 5,792,177 A | 8/1998 | Kaseda | 6,126,658 A | 10/2000 | Baker |
| 5,797,927 A | 8/1998 | Yoon | 6,152,923 A | 11/2000 | Ryan |
| 5,797,938 A | 8/1998 | Paraschac et al. | 6,162,220 A | 12/2000 | Nezhat |
| 5,797,941 A | 8/1998 | Schulze et al. | 6,174,309 B1 * | 1/2001 | Wrublewski et al. ............ 606/45 |
| 5,797,958 A | 8/1998 | Yoon | 6,179,834 B1 | 1/2001 | Buysse et al. |
| 5,800,449 A | 9/1998 | Wales | 6,179,837 B1 | 1/2001 | Hooven |
| 5,807,393 A | 9/1998 | Williamson, IV et al. | 6,183,467 B1 | 2/2001 | Shapeton et al. |
| 5,807,394 A * | 9/1998 | Sakai et al. ..................... 606/39 | 6,187,003 B1 | 2/2001 | Buysse et al. |
| 5,810,808 A | 9/1998 | Eggers | 6,190,386 B1 | 2/2001 | Rydell |
| 5,810,811 A | 9/1998 | Yates et al. | 6,193,718 B1 | 2/2001 | Kortenbach et al. |
| 5,810,877 A | 9/1998 | Roth et al. | 6,206,876 B1 | 3/2001 | Levine et al. |
| 5,814,043 A | 9/1998 | Shapeton | 6,206,877 B1 | 3/2001 | Kese et al. |
| 5,817,093 A | 10/1998 | Williamson, IV et al. | 6,217,602 B1 | 4/2001 | Redmon |
| 5,820,630 A | 10/1998 | Lind | 6,221,039 B1 | 4/2001 | Durgin et al. |
| 5,827,271 A | 10/1998 | Buysse et al. | 6,224,593 B1 | 5/2001 | Ryan et al. |
| 5,827,279 A | 10/1998 | Hughett et al. | 6,228,080 B1 | 5/2001 | Gines |
| 5,827,281 A | 10/1998 | Levin | 6,228,083 B1 | 5/2001 | Lands et al. |
| 5,827,323 A | 10/1998 | Klieman et al. | 6,267,761 B1 | 7/2001 | Ryan |
| 5,827,548 A | 10/1998 | Lavallee et al. | 6,270,497 B1 | 8/2001 | Sekino et al. |
| 5,833,690 A | 11/1998 | Yates et al. | 6,270,508 B1 | 8/2001 | Klieman et al. |
| 5,843,080 A | 12/1998 | Fleenor et al. | 6,273,887 B1 | 8/2001 | Yamauchi et al. |
| 5,849,022 A | 12/1998 | Sakashita et al. | 6,277,117 B1 | 8/2001 | Tetzlaff et al. |
| 5,853,412 A | 12/1998 | Mayenberger | 6,280,458 B1 | 8/2001 | Boche et al. |
| 5,860,976 A | 1/1999 | Billings et al. | 6,283,961 B1 | 9/2001 | Underwood et al. |
| 5,876,401 A | 3/1999 | Schulze et al. | D449,886 S | 10/2001 | Tetzlaff et al. |
| 5,882,567 A | 3/1999 | Cavallaro et al. | 6,302,424 B1 | 10/2001 | Gisinger et al. |
| 5,891,141 A | 4/1999 | Rydell | 6,319,451 B1 | 11/2001 | Brune |
| 5,891,142 A | 4/1999 | Eggers et al. | 6,322,561 B1 | 11/2001 | Eggers et al. |
| 5,893,863 A | 4/1999 | Yoon | 6,334,860 B1 | 1/2002 | Dorn |
| 5,893,875 A | 4/1999 | O'Connor et al. | 6,334,861 B1 | 1/2002 | Chandler et al. |
| 5,893,877 A | 4/1999 | Gampp, Jr. et al. | 6,345,532 B1 | 2/2002 | Coudray et al. |
| 5,902,301 A | 5/1999 | Olig | 6,350,264 B1 | 2/2002 | Hooven |
| 5,906,630 A | 5/1999 | Anderhub et al. | 6,352,536 B1 | 3/2002 | Buysse et al. |
| 5,908,420 A | 6/1999 | Parins et al. | 6,358,249 B1 | 3/2002 | Chen et al. |
| 5,908,432 A | 6/1999 | Pan | 6,358,268 B1 | 3/2002 | Hunt et al. |
| 5,911,719 A | 6/1999 | Eggers | D457,958 S | 5/2002 | Dycus et al. |
| 5,913,874 A | 6/1999 | Berns et al. | D457,959 S | 5/2002 | Tetzlaff et al. |
| 5,921,984 A | 7/1999 | Sutcu et al. | 6,387,094 B1 | 5/2002 | Eitenmuller |
| 5,925,043 A | 7/1999 | Kumar et al. | 6,391,035 B1 | 5/2002 | Appleby et al. |
| 5,935,126 A | 8/1999 | Riza | 6,398,779 B1 | 6/2002 | Buysse et al. |
| 5,944,718 A | 8/1999 | Austin et al. | 6,402,747 B1 | 6/2002 | Lindemann et al. |

| | | | |
|---|---|---|---|
| 6,409,725 B1 * | 6/2002 | Khandkar et al. ............ 606/45 |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,500,176 B1 | 12/2002 | Truckai et al. |
| 6,511,480 B1 | 1/2003 | Tetzlaff et al. |
| 6,514,252 B2 | 2/2003 | Nezhat et al. |
| 6,527,771 B1 | 3/2003 | Weadock et al. |
| 6,558,385 B1 | 5/2003 | McClurken et al. |
| 6,562,037 B2 | 5/2003 | Paton et al. |
| 6,585,735 B1 | 7/2003 | Frazier et al. |
| 6,602,252 B2 | 8/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,626,901 B1 | 9/2003 | Treat et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,177 B2 | 12/2003 | Truckai et al. |
| 6,660,072 B2 | 12/2003 | Chatterjee |
| 6,669,696 B2 | 12/2003 | Bacher et al. |
| 6,676,660 B2 | 1/2004 | Wampler et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,695,840 B2 | 2/2004 | Schulze |
| 6,702,810 B2 | 3/2004 | McClurken et al. |
| 6,726,068 B2 | 4/2004 | Miller |
| 6,726,686 B2 | 4/2004 | Buysse et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,757,977 B2 | 7/2004 | Dambal et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,775,575 B2 | 8/2004 | Bommannan et al. |
| 6,776,780 B2 | 8/2004 | Mulier et al. |
| 6,786,905 B2 * | 9/2004 | Swanson et al. ............ 606/32 |
| 6,790,217 B2 | 9/2004 | Schulze et al. |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,860,880 B2 | 3/2005 | Treat et al. |
| 6,887,240 B1 | 5/2005 | Lands et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| 6,942,662 B2 | 9/2005 | Goble et al. |
| 6,951,559 B1 * | 10/2005 | Greep ............................ 606/41 |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,977,495 B2 | 12/2005 | Donofrio |
| 6,979,786 B2 | 12/2005 | Aukland et al. |
| 6,994,707 B2 | 2/2006 | Ellman et al. |
| 6,994,709 B2 | 2/2006 | Iida |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,496 B2 | 5/2006 | Yamauchi |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,314,471 B2 | 1/2008 | Holman |
| 7,329,256 B2 | 2/2008 | Johnson et al. |
| 7,329,257 B2 | 2/2008 | Kanehira et al. |
| D564,662 S | 3/2008 | Moses et al. |
| 7,342,754 B2 | 3/2008 | Fitzgerald et al. |
| 7,344,268 B2 | 3/2008 | Jigamian |
| 7,367,976 B2 | 5/2008 | Lawes et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 * | 1/2003 | Dycus et al. .................... 606/48 |
| 2003/0018332 A1 | 1/2003 | Schmaltz et al. |
| 2003/0032956 A1 | 2/2003 | Lands et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 * | 6/2003 | Truckai et al. ................ 606/51 |
| 2003/0139741 A1 | 7/2003 | Goble et al. |

| Publication No. | Date | Inventor |
|---|---|---|
| 2003/0139742 A1 | 7/2003 | Wampler et al. |
| 2003/0158549 A1 | 8/2003 | Swanson |
| 2003/0181910 A1 | 9/2003 | Dycus et al. |
| 2003/0195513 A1* | 10/2003 | Truckai et al. .................. 606/51 |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0162557 A1 | 8/2004 | Tetzlaff et al. |
| 2004/0193153 A1 | 9/2004 | Sarter et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0021025 A1 | 1/2005 | Buysse et al. |
| 2005/0021027 A1 | 1/2005 | Shields et al. |
| 2005/0033278 A1 | 2/2005 | McClurken et al. |
| 2005/0055021 A1* | 3/2005 | Clement et al. .................. 606/45 |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0149017 A1 | 7/2005 | Dycus |
| 2005/0149151 A1 | 7/2005 | Orszulak et al. |
| 2005/0154385 A1* | 7/2005 | Heim et al. ...................... 606/41 |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0064085 A1 | 3/2006 | Schechter et al. |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0045947 A1 | 2/2008 | Johnson et al. |
| 2008/0058802 A1 | 3/2008 | Couture et al. |
| 2008/0082100 A1 | 4/2008 | Orton et al. |

FOREIGN PATENT DOCUMENTS

| | | |
|---|---|---|
| DE | 2415263 | 10/1975 |
| DE | 2627679 | 1/1977 |
| DE | 8712328 | 3/1988 |
| DE | 4303882 | 8/1994 |
| DE | 29616210 | 1/1997 |
| DE | 19608716 | 4/1997 |
| DE | 19751106 | 5/1998 |
| DE | 19751108 | 5/1999 |
| EP | 0364216 A1 | 4/1990 |
| EP | 518230 A1 | 12/1992 |
| EP | 0 541 930 B1 | 5/1993 |
| EP | 0572131 | 12/1993 |
| EP | 584787 A1 | 3/1994 |
| EP | 0589453 A2 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1301135 A | 4/2003 |
| EP | 1330991 A1 | 7/2003 |
| EP | 1486177 A2 | 6/2004 |

| | | |
|---|---|---|
| EP | 1472984 A1 | 11/2004 |
| EP | 1527747 A2 | 5/2005 |
| EP | 1530952 A1 | 5/2005 |
| EP | 1532932 A1 | 5/2005 |
| EP | 1535581 A2 | 6/2005 |
| EP | 1609430 A1 | 12/2005 |
| EP | 1632192 A1 | 3/2006 |
| EP | 1645238 A1 | 4/2006 |
| EP | 1645240 A2 | 4/2006 |
| EP | 1707143 A1 | 10/2006 |
| GB | 2214430 A | 6/1989 |
| GB | 2213416 | 8/1989 |
| JP | 501068 | 9/1984 |
| JP | 502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 94/08524 A | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/40857 | 8/1999 |
| WO | WO 99/40861 | 8/1999 |
| WO | WO 99/51158 | 10/1999 |
| WO | WO 99/66850 A | 12/1999 |
| WO | WO 00/24330 | 5/2000 |
| WO | WO 00/24331 | 5/2000 |
| WO | WO 00/41638 | 7/2000 |
| WO | WO 00/47124 | 8/2000 |
| WO | WO 00/53112 | 9/2000 |
| WO | WO 01/17448 A | 3/2001 |
| WO | WO 01/54604 | 8/2001 |
| WO | WO 02/07627 | 1/2002 |
| WO | WO 02/067798 A1 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/090630 A3 | 11/2003 |
| WO | WO 03/101311 | 12/2003 |
| WO | WO 2004/032776 A1 | 4/2004 |
| WO | WO 2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 A1 | 1/2005 |
| WO | WO 2005/004735 | 1/2005 |
| WO | WO 2005/110264 | 11/2005 |

OTHER PUBLICATIONS

Bergdahl et al. "Studies on Coagulation and the Development of an Automatic Computerized Bipolar Coagulator" J. Neurosurg, vol. 75, Jul. 1991, pp. 148-151.

Kennedy et al. "High-burst-strength, feedback-controlled bipolar vessel sealing" Surgical Endoscopy (1998) 12: 876-878.

Peterson et al. "Comparison of Healing Process Following Ligation with Sutures and Bipolar Vessel Sealing" Surgical Technology International (2001).

Linehan et al. "A Phase I Study of the LigaSure Vessel Sealing System in Hepatic Surgery" Section of HPB Surger, Washington University School of Medicine, St. Louis MO, Presented at AHPBA, Feb. 2001.

Johnson et al. "Evaluation of the LigaSure Vessel Sealing System in Hemorrhoidectormy" American College of Surgeons (ACS) Clinicla Congress Poster (2000).

Sayfan et al. "Sutureless Closed Hemorrhoidectomy: A New Technique" Annals of Surgery vol. 234 No. 1 Jul. 2001 pp. 21-24.

Heniford et al. "Initial Results with an Electrothermal Bipolar Vessel Sealer" Surgical Endoscopy (2000) 15:799-801.

Heiniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics FIGO World Congress 2000, Washington, D.C.

Levy et al. "Use of a New Energy-based Vessel Ligation Device During Vaginal Hysterectomy" Int'l Federation of Gynecology and Obstetrics (FIGO) World Congress 1999.

Crawford et al. "Use of the LigaSure Vessel Sealing System in Urologic Cancer Surger" Grand Rounds in Urology 1999 vol. 1 Issue 4 pp. 10-17.

Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 89, 154-157.

"Innovations in Electrosurgery" Sales/Product Literature; Dec. 31, 2000.

LigaSure Vessel Sealing System, the Seal of Confidence in General, Gynecologic, Urologic, and Laparaoscopic Surgery Sales/Product Literature; Jan. 2004.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.

"Reducing Needlestick Injuries in the Operating Room" Sales/Product Literature 2001.

Chung et al., "Clinical Experience of Sutureless Closed Hemorrhoidectomy with LigaSure" Diseases of the Colon & Rectum vol. 46, No. 1 Jan. 2003.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Paul G. Horgan, "A Novel Technique for Parenchymal Division During Hepatectomy" The American Journal of Surgery, vol. 181, No. 3, Apr. 2001 pp. 236-237.

W. Scott Helton, "LigaSure Vessel Sealing System: Revolutionary Hemostasis Product for General Surgery" Sales/Product Literature 1999.

Michael Choti, "Abdominoperineal Resection with the LigaSure Vessel Sealing System and LigaSure Atlas 20 cm Open Instrument" Innovations That Work, Jun. 2003.

Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With the LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing for Hemostasis During Gynecologic Surgery" Sales/Product Literature 1999.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
E. David Crawford "Evaluation of a New Vessel Sealing Device in Urologic Cancer Surgery" Sales/Product Literature 2000.
Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar electrothermal Vessel Sealing Device in Hemorrhoidectomy" Sales/Product Literature; Jan. 2004.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated Oct. 31, 2000.
Int'l Search Report EP 98958575.7 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04013772 dated Apr. 1, 2005.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended- EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008779.8 dated Jun. 13, 2006.
Int'l Search Report EP 1683496 dated Jun. 13, 2006.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.

* cited by examiner

ABLATIVE MATERIAL FOR USE WITH TISSUE TREATMENT DEVICE

BACKGROUND

The present disclosure relates to an electrode assembly for use with electrosurgical instruments and, more particularly, the present disclosure relates to an electrode assembly including an electrically conductive tissue engaging surface having an ablative material disposed thereon to reduce tissue adhesion during activation.

TECHNICAL FIELD

Open or endoscopic electrosurgical forceps utilize both mechanical clamping action and electrical energy to effect hemostasis. The electrode of each opposing jaw members is charged to a different electric potential such that when the jaw members grasp tissue, electrical energy can be selectively transferred through the tissue. A surgeon can either seal, cauterize, ablate, coagulate/desiccate, cut, dissect and/or simply reduce or slow bleeding, by controlling the intensity, frequency and duration of the electrosurgical energy applied between the electrodes and through the tissue. For the purposes herein, "coagulation" is defined as a process of desiccating tissue wherein the tissue cells are ruptured and dried. "Vessel sealing" is defined as the process of liquefying the collagen in the tissue so that it reforms into a fused mass with significantly-reduced demarcation between the opposing tissue structures (opposing walls of the lumen). Coagulation of small vessels is usually sufficient to permanently close them. Larger vessels need to be sealed to assure permanent closure.

To effectively seal tissue or vessels, especially thick tissue and large vessels, two predominant mechanical parameters must be accurately controlled: 1) the pressure applied to the vessel, which is ideally between about 3 kg/cm2 to about 16 kg/cm2; and 2) the gap distance between the conductive tissue contacting surfaces (between about 0.001 and about 0.006 inches).

During any electrosurgical procedure involving cauterization, coagulation, sealing, ablation, dissection and/or cutting there is a possibility that tissue will adhere or stick to the electrically conductive surfaces. Previously developed devices have been successful in reducing tissue adhesion by manufacturing or coating the electrically conductive surfaces with non-stick materials, such as nickel-chrome, and nitride coatings, such as chromium nitride, MedCoat 2000, Inconel 600 and tin-nickel. Nitride coatings (e.g., TiN, ZrN, TiAlN, and CrN) have been particularly successful in producing non-stick properties. For example, CrN has been found to be particularly useful for non-stick purposes due to its overall surface properties and optimal performance. Other classes of materials have also been found to reduce overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces and made from or coated with Ni200, Ni201 (~100% Ni) also showed improved non-stick performance over typical bipolar stainless steel electrodes. As can be appreciated, these properties are desirable for electrosurgical instrumentation that are naturally exposed to high temperatures, high RF energy and organic matter.

SUMMARY

The present disclosure relates to an electrosurgical instrument for treating tissue and includes a housing having at least one tissue treating member attached thereto. The tissue treating member includes an electrically conductive tissue contacting surface connected to a source of electrosurgical energy such that the tissue contacting surface is capable of conducting electrosurgical energy to tissue. An energy conductive, ablative material is disposed on the electrically conductive tissue contacting surface and is configured to at least partially deplete during electrosurgical activation to reduce tissue adhesion. The instrument may be any one of a variety of instruments including bipolar instruments, monopolar instrument, ablation instruments, thermal treatment instruments, ultrasonic instruments, microwave instruments and radiofrequency instruments. The energy conductive, ablative material may include one or more materials selected from a group of materials consisting of: fiberglass material impregnated with phenolic resin and silica powder; combinations of phenolic resin, polyamide and silica powder; silicone elastomer, rayon-based carbon material, ceramic-forming polymer, etc. The energy conductive, ablative material may also be sterilizeable for a pre-determined number of sterilization cycles.

The present disclosure also relates to an electrode assembly for use with an electrosurgical instrument which includes a pair of opposing first and second jaw members being movable relative to one another from a first position wherein the jaw members are disposed in spaced relation relative to one another to a second position wherein the jaw members cooperate to grasp tissue therebetween. Each jaw member includes an electrically conductive tissue contacting surface which is connected to a source of electrosurgical energy such that the tissue contacting surfaces are capable of conducting electrosurgical energy through the tissue held therebetween. At least one of the tissue contacting surfaces includes an energy conductive, ablative material disposed thereon which is configured or formulated to at least partially deplete during electrosurgical activation to reduce tissue adhesion.

In one embodiment according to the present disclosure, the energy conductive, ablative material is applied to the at least one electrically conductive surface prior to or during electrosurgical application in the form of a gel or a liquid material. The ablative material may also be formed on the conductive surfaces in a solid form during a manufacturing step. In another embodiment, a sensor may also be included which monitors the depletion rate of the energy conductive, ablative material and relays information relating to the depletion rate back to the electrosurgical energy source. The electrosurgical energy source may include an audible and/or visual indicator which warns a user when the sensor relays information relating to the depletion rate which falls within a predefined threshold.

In yet another embodiment, the electrosurgical energy source measures the changes in electrical properties of the electrically conductive surface(s) corresponding to the amount of energy conductive, ablative material loss over time and modifies the electrosurgical energy delivery based thereon to maintain proper energy delivery during electrosurgery.

The present disclosure also relates to an electrode assembly for use with an instrument for sealing tissue which includes a pair of opposing first and second jaw members movable relative to one another from a first position wherein the jaw members are disposed in spaced relation relative to one another to a second position wherein the jaw members cooperate to grasp tissue therebetween. Each jaw member includes an electrically conductive tissue contacting surface connected to a source of electrosurgical energy such that the tissue contacting surfaces are capable of conducting electrosurgical energy through the tissue held therebetween to effect a seal. At least one of the tissue contacting surfaces of one of the jaw members including an energy conductive, ablative material disposed thereon which is configured to at least partially burn off during electrosurgical activation to reduce tissue adhesion. The source of electrosurgical energy includes an algorithm which monitors at least one electrical property of the electrically conductive surface(s) and continuously modifies energy delivery based thereon.

The present disclosure also relates to a method for sealing tissue and includes the initial step of providing an electrode assembly including: a pair of opposing first and second jaw members, each jaw member including an electrically conductive tissue contacting surface adapted to connect to a source of electrosurgical energy such that the tissue contacting surfaces are capable of conducting electrosurgical energy through tissue held therebetween to effect a tissue seal; and at least one of the tissue contacting surfaces of one of the jaw members including an energy conductive, ablative material disposed thereon, the energy conductive, ablative material being configured to at least partially burn off during electrosurgical activation to reduce tissue adhesion.

The method also includes the steps of: moving the jaw member relative to one another to grasp tissue therebetween; applying electrosurgical energy to the tissue contacting surfaces to conduct electrosurgical energy through tissue held therebetween; and monitoring at least one electrical property of the at least one electrically conductive surface and continuously modifying energy delivery based thereon.

In one embodiment, the electrode assembly further includes a sensor and the method further includes the steps of: monitoring a depletion rate of the energy conductive, ablative material with the sensor; and relaying information relating to the depletion rate back to the source of electrosurgical energy.

BRIEF DESCRIPTION OF THE DRAWINGS

Various embodiments of the present disclosure are described herein with reference to the drawings wherein.

DETAILED DESCRIPTION

Figure 1A:
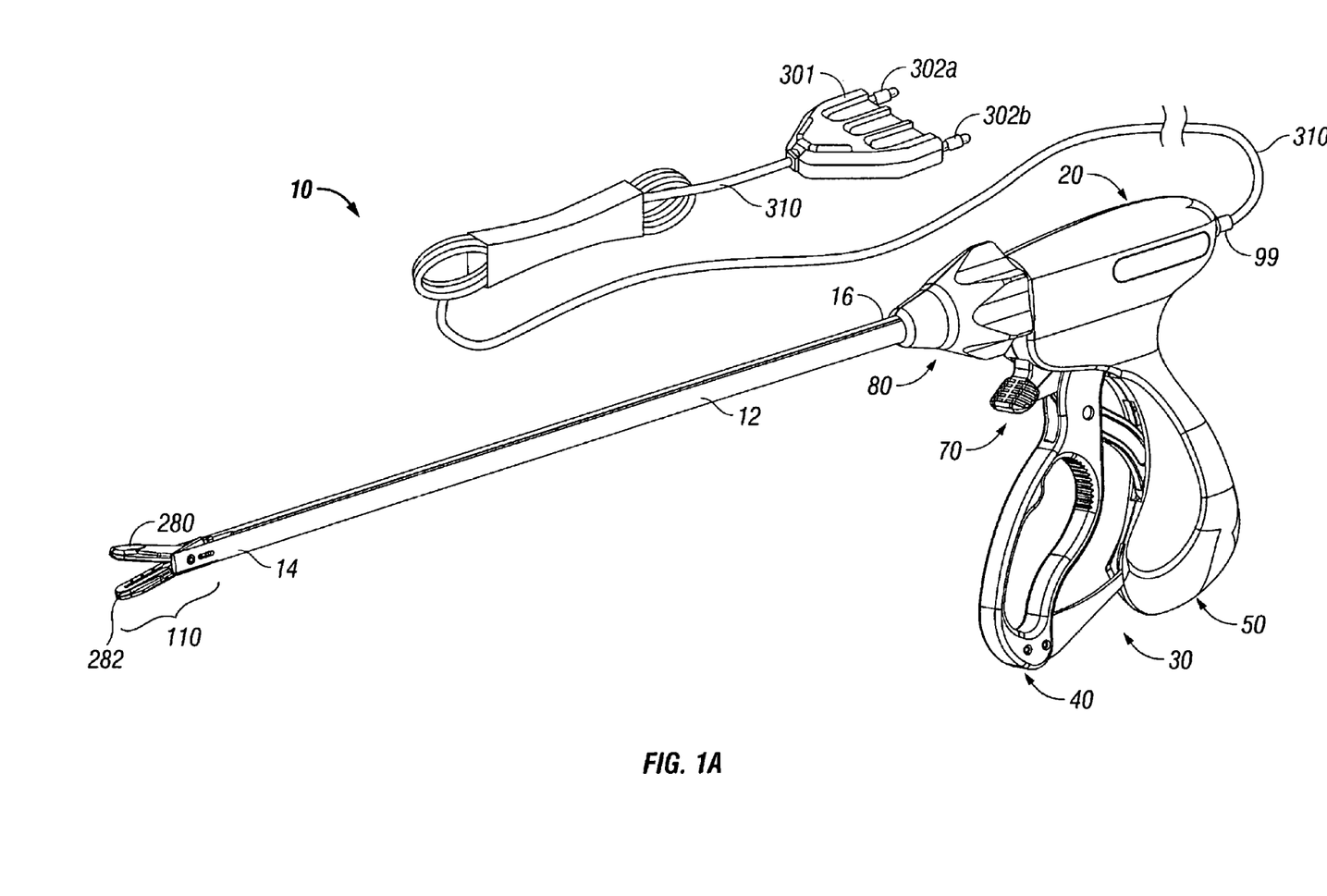
FIG. 1A is a right, perspective view of an endoscopic bipolar forceps showing a housing, a shaft and an electrode assembly according to the present disclosure.
Figure 1B:
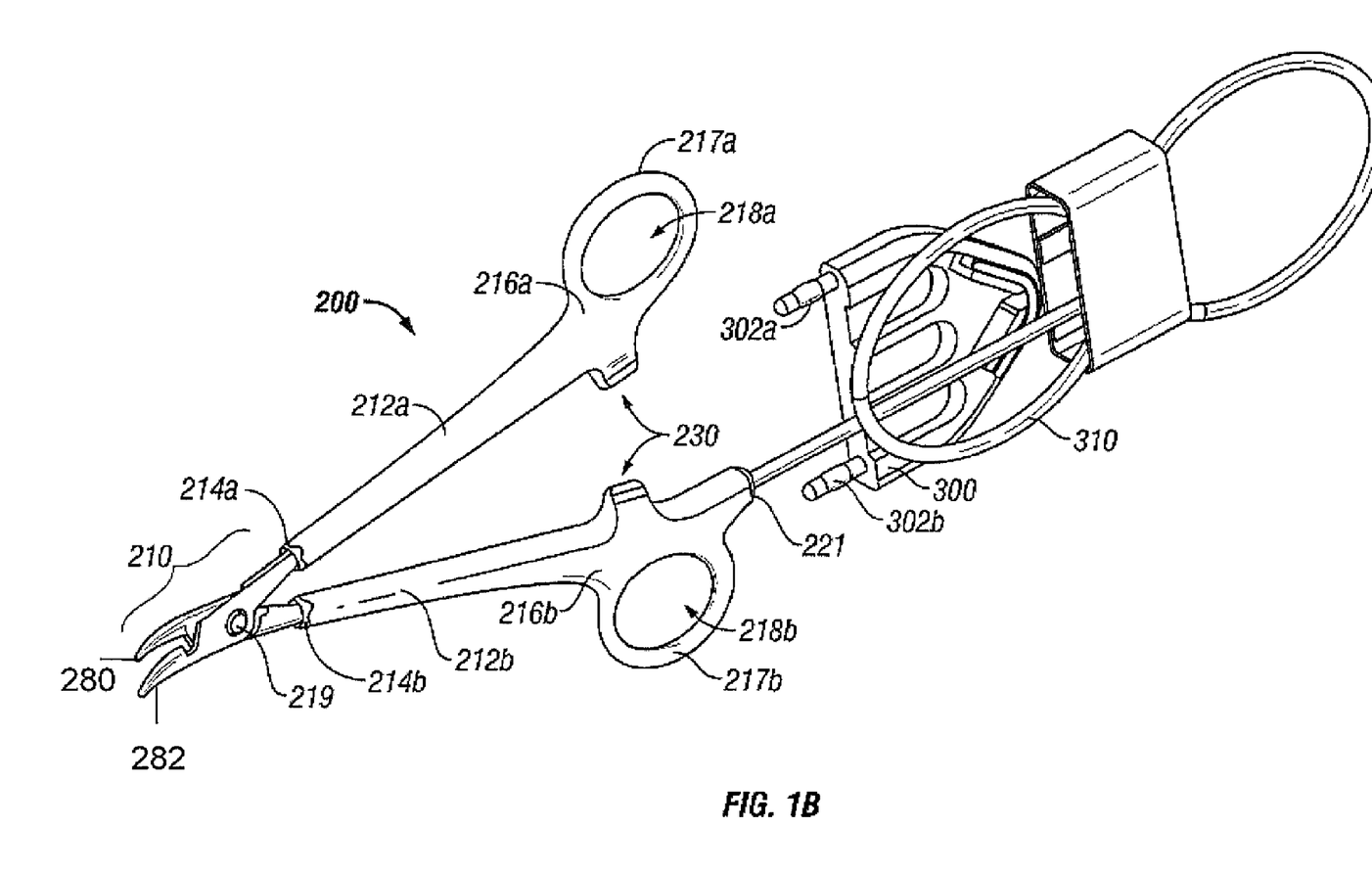
FIG. 1B is a right, perspective view of an open bipolar forceps having an electrode assembly according to the present disclosure.

Referring now to FIGS. 1A and 1B, an endoscopic bipolar forceps 10 is shown for use with various surgical procedures. Forceps 10 generally includes a housing 20, a handle assembly 30, a rotating assembly 80, a trigger assembly 70 and an electrode assembly 110 that mutually cooperate to grasp, seal and divide tubular vessels and vascular tissue. Although FIG. 1A depicts a bipolar forceps 10 for use in connection with endoscopic surgical procedures and FIG. 1B depicts an open forceps 200 for use in connection with traditional open surgical procedures, other suitable endoscopic or open electrosurgical instruments are contemplated, that include electrodes or electrically conductive surfaces that are applicable to the presently described disclosure, e.g., electrosurgical knives, electrosurgical pencils, electrosurgical scissors, ablation instruments, thermal treatment instruments, ultrasonic instruments, microwave instruments and radiofrequency instruments.

For the purposes herein, any of the aforementioned instruments may be utilized with the present disclosure. Moreover, either an endoscopic instrument or an open instrument may be utilized with the presently disclosed electrosurgical instrument and electrode assembly described herein. Obviously, and with particular respect to an electrosurgical forceps, different electrical and mechanical connections and considerations apply to each particular type of instrument; however, the novel aspects with respect to the electrosurgical instrument and electrode assembly and its operating characteristics remain generally consistent with respect to both the open or endoscopic designs.

More particularly, forceps 10 includes a shaft 12 that has a distal end 14 dimensioned to mechanically engage the electrode assembly 110 and a proximal end 16 that mechanically engages the housing 20. The shaft 12 may be bifurcated at the distal end 14 thereof to receive the electrode assembly 110. The proximal end 16 of shaft 12 mechanically engages the rotating assembly 80 to facilitate rotation of the electrode assembly 110. In the drawings and in the descriptions that follow, the term "proximal", as is traditional, will refer to the end of the forceps 10 that is closer to the user, while the term "distal" will refer to the end that is further from the user.

Figure 3:
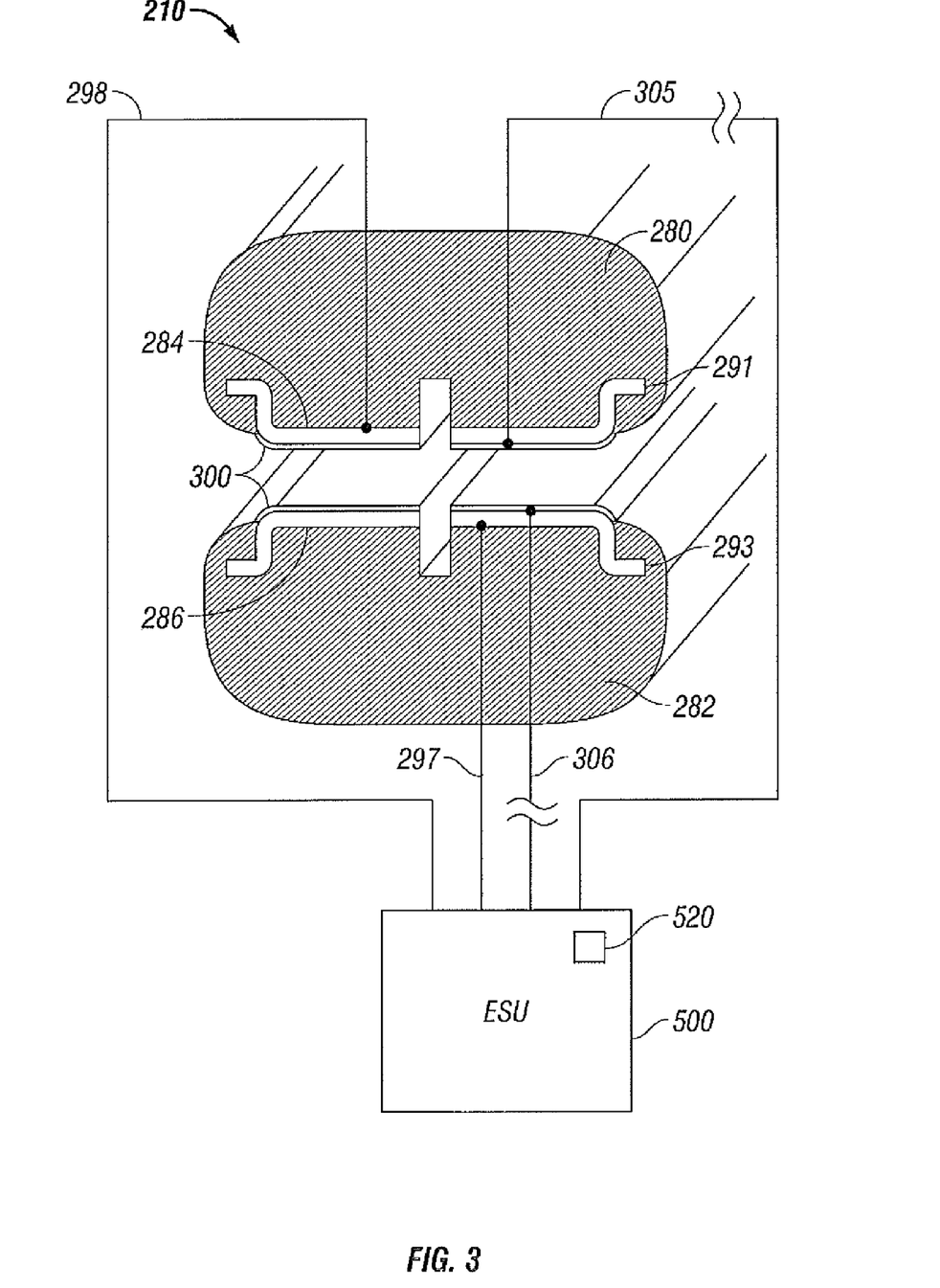
FIG. 3 is an enlarged front view taken along line 3-3 of FIG. 2 showing schematic electrical connections to the tissue contacting surfaces of the jaw members.

As best seen in FIG. 1A, forceps 10 also includes an electrical interface or plug 301 that connects the forceps 10 to a source of electrosurgical energy, e.g., an electrosurgical generator 500 (FIG. 3). Plug 301 includes a pair of prong members 302a and 302b that are dimensioned to mechanically and electrically connect the forceps 10 to the electrosurgical generator 500 (FIG. 3). An electrical cable 310 extends from the plug 301 to a sleeve 99 that securely connects the cable 310 to the forceps 10. Cable 310 is internally divided within the housing 20 to transmit electrosurgical energy through various electrical feed paths to the electrode assembly 110.

Handle assembly 30 includes a fixed handle 50 and a movable handle 40. Fixed handle 50 is integrally associated with housing 20 and handle 40 is movable relative to fixed handle 50 to actuate a pair of opposing jaw members 280 and 282 of the electrode assembly 110 as explained in more detail below. Movable handle 40 and trigger assembly 70 are preferably of unitary construction and are operatively connected to the housing 20 and the fixed handle 50 during the assembly process.

As mentioned above, electrode assembly 110 is attached to the distal end 14 of shaft 12 and includes a pair of opposing jaw members 280 and 282. Movable handle 40 of handle assembly 30 imparts movement of the jaw members 280 and 282 from an open position wherein the jaw members 280 and 282 are disposed in spaced relation relative to one another, to a clamping or closed position wherein the jaw members 280 and 282 cooperate to grasp tissue therebetween.

Forceps 10 may be designed such that it is fully or partially disposable depending upon a particular purpose or to achieve a particular result. For example, electrode assembly 110 may be selectively and releasably engageable with the distal end 14 of the shaft 12 and/or the proximal end 16 of shaft 12 may be selectively and releasably engageable with the housing 20 and the handle assembly 30. In either of these two instances, the forceps 10 would be considered "partially disposable" or "reposable", i.e., a new or different electrode assembly 110 (or electrode assembly 110 and shaft 12) selectively replaces the old electrode assembly 110 as needed.

Referring now to FIG. 1B, an open forceps 200 is shown which includes a pair of elongated shaft portions 212a each having a proximal end 216a and 216b, respectively, and a distal end 214a and 214b, respectively. The forceps 200 includes electrode assembly 210 that attaches to distal ends 214a and 214b of shafts 212a and 212b, respectively. Electrode assembly 210 includes opposing jaw members 280 and 282 which are pivotably connected about a pivot pin 219.

Each shaft 212a and 212b includes a handle 217a and 217b disposed at the proximal end 216a and 216b thereof that each defines a finger hole 218a and 218b, respectively, therethrough for receiving a finger of the user. As can be appreciated, finger holes 218a and 218b facilitate movement of the shafts 212a and 212b relative to one another, which, in turn, pivot the jaw members 280 and 282 from an open position wherein the jaw members 280 and 282 are disposed in spaced relation relative to one another to a clamping or closed position wherein the jaw members 280 and 282 cooperate to grasp tissue therebetween. A ratchet 230 may be included for selectively locking the jaw members 280 and 282 relative to one another at various positions during pivoting.

Each position associated with the cooperating ratchet interfaces 230 holds a specific, i.e., constant, strain energy in the shaft members 212a and 212b, which, in turn, transmits a specific closing force to the jaw members 280 and 282. The ratchet 230 may include graduations or other visual markings which enable the user to easily and quickly ascertain and control the amount of closure force desired between the jaw members 280 and 282.

One of the shafts, e.g., 212b, includes a proximal shaft connector/flange 221 that is designed to connect the forceps 200 to a source of electrosurgical energy, such as an electrosurgical generator 342. More particularly, flange 221 mechanically secures electrosurgical cable 310 to the forceps 200 such that the user may selectively apply electrosurgical energy as needed. The proximal end of the cable 310 includes a similar plug 301 as described above with respect to FIG. 1A. The interior of cable 310 houses a pair of leads that conduct different electrical potentials from the electrosurgical generator 500 (FIG. 3) to the jaw members 280 and 282 as explained below with respect to FIG. 2.

The jaw members 280 and 282 are generally symmetrical and include similar component features that cooperate to permit facile rotation about pivot 219 to effect the grasping and sealing of tissue. Each jaw member 280 and 282 includes an electrically conductive tissue contacting surface 284 and 286, respectively, which cooperate to engage the tissue during sealing and cutting. One of the jaw members may include a cutting element 295 disposed therein, that is explained in detail below.

Figure 2:
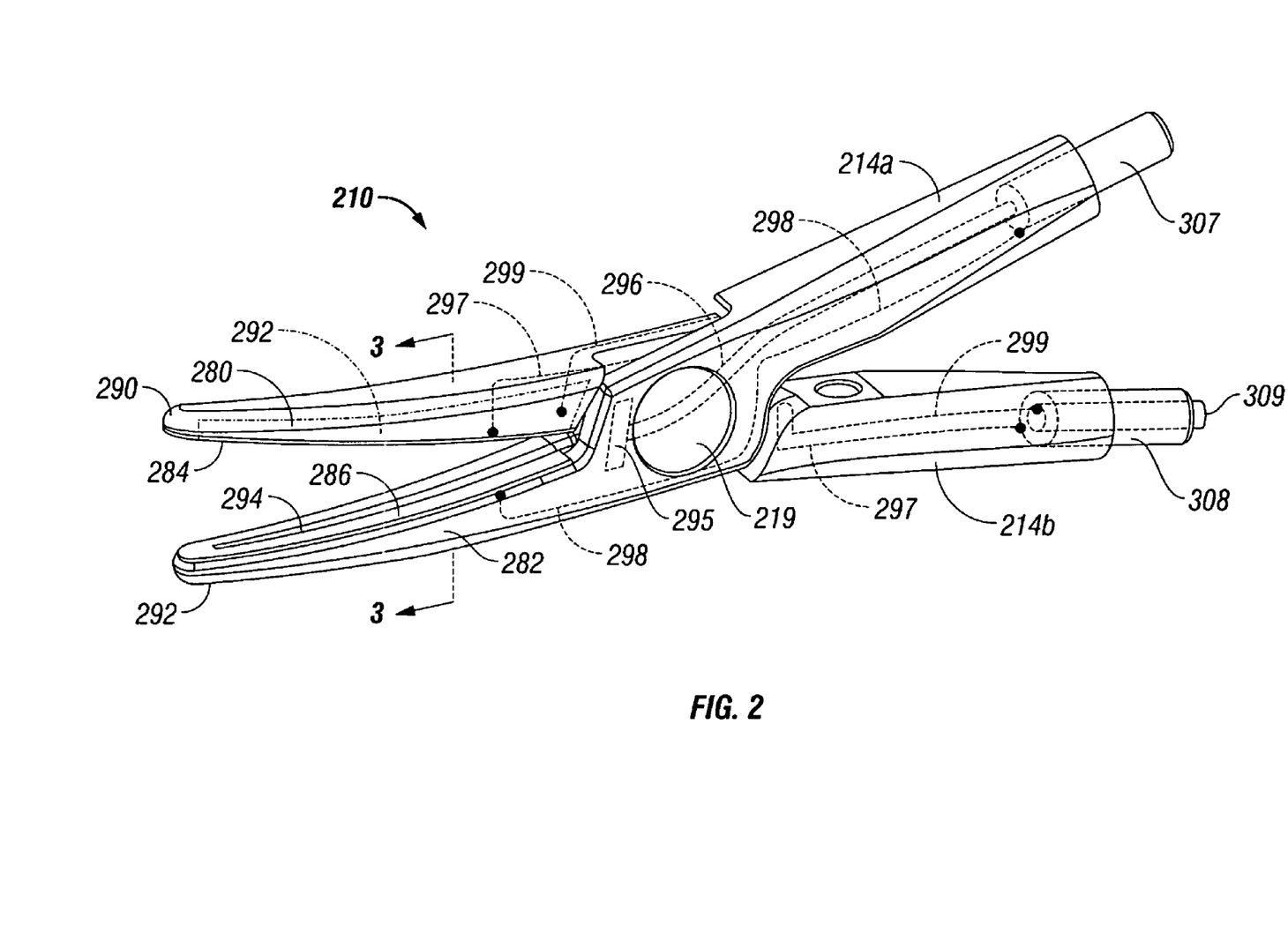
FIG. 2 is an enlarged view of the electrode assembly of FIG. 1B showing tissue contacting surfaces of the electrode assembly.

As best shown in FIGS. 1B and 2, the various electrical connections of the electrode assembly 210 are preferably configured to provide electrical continuity to the tissue contacting surfaces 284 and 286. More particularly, two connector pins 307 and 308 are located at the proximal end of the electrode assembly 210. Connections 307 and 308 are preferably mechanically and electrically interfaced with corresponding electrical connections (not shown) disposed within shafts 212a and 212b, respectively. As can be appreciated, the electrical connectors 307 and 308 may be permanently soldered to the shafts 212a and 212b during the assembly process of a disposable instrument or, alternatively, selectively removable for use with a reposable instrument.

Connector 307 is internally connected to lead 298 disposed within the electrode assembly 210 to provide electrical continuity to tissue contacting surface 286 of jaw member 282. Likewise, connector 308 is internally connected to lead 297 and provides electrical continuity to tissue contacting surface 284 of jaw member 280. The electrode assembly 210 may also be configured to include a knife 295, which is selectively translatable within a corresponding jaw channel 294 disposed in jaw member 282 (and/or jaw member 280). In this instance, connector 308 may also include a second electrical interface 309 that provides electrical continuity to a cutting element through electrode assembly 210. Interfaces 308 and 309 are preferably dielectrically insulated from one another to allow selective and independent activation of either the tissue contacting surface 284 or the cutting element.

Alternatively, the electrode assembly 210 may include a single connector, e.g., 308, which includes an internal switch to allow selective and independent activation of the tissue contacting surface 284 and the cutting element. Preferably, leads 297, 298 and 299 (and/or conductive pathways) do not encumber the movement of the jaw members 280 and 282 relative to one another during the manipulation and grasping of tissue. Likewise, the movement of the jaw members 280 and 282 do not unnecessarily strain the lead connections 297, 298 and 299.

As best seen in FIG. 2 jaw members 280 and 282 both include conductive tissue contacting surfaces 284 and 286, respectively, disposed along substantially the entire longitudinal length thereof (i.e., extending substantially from the proximal to distal end of each respective jaw member 280 and 284). The tissue contacting surfaces are disposed in general vertical opposition relative to one another to facilitate grasping of tissue and tissue treatment. Tissue contacting surfaces 284 and 286 may be attached to the jaw member 280 and 284 by stamping, by overmolding, by casting, by overmolding a casting, by coating a casting, by overmolding a stamped electrically conductive sealing plate and/or by overmolding a metal injection molded seal plate. All of these manufacturing techniques can be employed to produce jaw member 280 and 284 having electrically conductive tissue contacting surfaces 284 and 286 disposed thereon for contacting and grasping tissue.

The electrically conductive sealing surfaces 284 and 286 may also each include a pinch trim 291 and 293 that facilitates secure engagement of the electrically conductive surfaces 284 and 286 to the jaw members 280 and 282 and also simplifies the overall manufacturing process. The jaw members 280 and 282 are configured to include an insulator or insulative material 290 and 292, respectively, disposed on the outer periphery and substantially along the entire longitudinal length thereof. Each insulative material 290 and 292 is configured to house respective tissue contacting surfaces 284 and 286. Each electrically conductive tissue sealing surface 284 and 286 may also include an outer peripheral edge that has a radius and the respective insulative material 290 and 292 of each jaw member 280 and 282 meets the electrically conductive sealing surface 284 and 286 along an adjoining edge, which is generally tangential to the radius and/or meets along the radius.

One or both of the insulators 290 and 292 may be made from a ceramic material due to its hardness and inherent ability to withstand high temperature fluctuations. Alternatively, one or both of the insulators 290 and 292 may be made from a material having a high Comparative Tracking Index (CTI) having a value in the range of about 300 to about 600 volts. Examples of high CTI materials include nylons and syndiotactic polystryrenes, such as QUESTRA® manufactured by DOW Chemical. Other materials may also be utilized either alone or in combination, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

As mentioned above, and with particular respect to tissue sealing, two mechanical factors play an important role in determining the resulting thickness of the sealed tissue and effectiveness of a tissue seal, i.e., the pressure applied between opposing jaw members 280 and 282 and the gap distance "G" between the opposing tissue contacting surfaces 284 and 286 during the sealing process. The gap distance "G" during sealing ranges from about 0.001 inches to about 0.006 inches and, preferably, between about 0.002 inches and about 0.003 inches. The clamping pressure between the opposing tissue contacting surfaces 284 and 286 is preferably between about 3 kg/cm$^2$ to about 16 kg/cm$^2$.

As best seen in the cross section view of FIG. 3, at least one of the electrically conductive tissue contacting surfaces 284 and 286 includes an energy conductive, ablative material 300 disposed thereon. With particular respect to vessel sealing, as shown in the illustrative example of FIG. 3, each electrically conductive tissue contacting surface 284 and 286 may include an ablative material 300 disposed thereon that is designed to burn off or deplete during electrical application. The burning off of ablative material 300 essentially keeps the tissue from sticking or adhering to the tissue contacting surfaces 284 and 286. More particularly, as electrosurgical energy is supplied to the tissue contacting surfaces 284 and 286 for treating tissue, the formulation of the ablative material 300 reacts to the electrical and/or thermal energy created by the electrosurgical activation and essentially burns off or steadily depletes, which prevents tissue from adhering to the tissue surfaces 284 and 286.

The ablative material 300 may be formulated or designed to essentially "burn off" or deplete during any type of energy application, e.g., ultrasonic, microwave, thermal and/or radiofrequency energy application, or based on a specific type of energy application, e.g., RF energy application, to reduce tissue adherence to the tissue contacting surfaces 284 and 286. For example, the ablative material 300 may be formulated or designed to burn off due to the heat build-up on the tissue contacting surfaces 284 and 286 or, in other instances, based on thermo-mechanical operating parameters (e.g., heat and vibration) and/or thermo-electrical operating parameters (microwave).

The ablative material may be formulated or formed from a combination of one or more of the following materials fiberglass material impregnated with phenolic resin and silica powder; combinations of phenolic resin, polyamide and silica powder; silicone elastomer, rayon-based carbon material, ceramic-forming polymer, or other ceramics, polymers, ceramic, metal, silica, phenol, fiberglass, etc.

In addition, the ablative material 300 may be manually applied to the tissue contacting surfaces prior to tissue treatment in the form of a liquid or gel or the ablative material may be added to the tissue contacting surfaces during a manufacturing step. In the latter instance, the material may be applied to the tissue surfaces initially as a liquid or gel material and allowed to harden prior to application. Additional ablative material 300 may be re-applied during use as needed when tissue sticking is apparent. Alternatively, the ablative material 300 may be a solid layer and applied during a manufacturing step or applied by a surgeon prior to electrical activation like tape or a boot over the tissue contacting surfaces 284 and 286.

In one embodiment, the ablative material is formulated or formed from a biocompatible substance. The ablative material 300 may also include one or more coagulants or antibodies or antibiotics, which may be absorbed by the tissue during treatment. In the case of complete burn off, these formulations may burn off into a gaseous state which is readily absorbed by the tissue to promote healing. In instances where the ablative material does not burn off into a gaseous state, but burns off into a liquid, semi-liquid (e.g., oozing) or solid state (e.g., "flake off"), the ablative material 300 is not harmful to tissue and may also be formulated or designed to promote healing.

With continued reference to FIG. 3, the electrode assembly 210 may also include one or more sensors 305 and 306 connected to respective tissue contacting surfaces 284 and 286 that are configured to monitor the burn off rate of the ablative material from the tissue contacting surfaces 284 and 286. More particularly, the sensors 305 and 306 monitor the rate at which the ablative material 300 is depleted or reduced in thickness or quality (e.g., the so-called "depletion rate" of the ablative material 300) and relay information relating to the depletion rate back to the generator 500. The generator 500 may be designed to include one or more algorithms that monitor at least one electrical property of the electrically conductive tissue surface(s) and continuously modify energy delivery based thereon.

The generator 500 may also be designed to include one or more algorithms that both monitor the depletion rate and continuously adjust the electrosurgical output of the generator 500 based thereon. The generator may include one or more audible and/or visual indicators 520 that warn a user when the sensor relays information relating to the depletion rate or overall depletion loss that falls within a predefined threshold. For example, the generator 500 may automatically shut off when the depletion rate or the overall depletion loss is likely to lead to tissue adherence. In another example, the generator measures the changes in electrical properties of the tissue surface corresponding to the amount of ablative material loss over time and modifies the electrosurgical energy delivery based thereon to maintain proper energy delivery during electrosurgery.

The ablative material 300 may be formulated or designed for a specific number of electrical activations for disposable electrosurgical instruments or the ablative material 300 may be formulated to withstand a specified number of sterilization cycles for reposable or reusable instruments.

In one envisioned embodiment, the ablative material 300 may be formulated to naturally burn off or deplete over time simply based on exposure to the atmosphere. In this instance, the ablative material may be applied to the tissue contacting surface or surfaces 284 and 286 and hermetically sealed during a manufacturing step or may be applied to the tissue contacting surfaces 284 and 286 just prior to electrical activation. In the latter instance, additional ablative material 300 may be re-applied during use as needed when tissue sticking is apparent. As can be appreciated, this would allow the surgeon to grasp and manipulate tissue without sticking and not require the surgeon to activate the instrument if there is tissue.

With particular reference to FIG. 2 and as mentioned above, one of the jaw members 280 may include an electrically conductive cutting element 295 that is selectively translatable within channel 294 defined in one or both the jaw members 280 and 286 to cut tissue prior to, simultaneously with or after tissue treatment. The cutting element 295 may be simply mechanical or may be electrically conductive. In the latter instance, the cutting element 295 may include the same ablative material 300 disposed thereon. The cutting element 295 may also include a different ablative material selected from the list identified above depending upon a specific purpose. As can be appreciated, by applying the ablative material to the cutting element 295, tissue adherence may be reduced during an electromechanical cutting phase of operation of the instrument. A suitable switch (not shown) may be employed to allow the surgeon to selectively activate tissue contacting surfaces 284 and 286 or the cutting element 295 independently of one another.

From the foregoing and with reference to the various figure drawings, those skilled in the art will appreciate that certain modifications can also be made to the present disclosure without departing from the scope of the present disclosure. For example, although an open instrument is described and shown having the ablative material 300 disposed thereon, it is envisioned that endoscopic electrosurgical instruments may be similarly configured to include the ablative material and the above-described appurtenances relating thereto (i.e., sensors, algorithms, etc.). Moreover, it is contemplated that other electrosurgical instruments may be configured to include the presently-disclosed ablative material 300, e.g., microwave instruments, ablation instruments, scissors, ultrasonic instruments, electrosurgical pencils, resistively heated instruments, knives and scalpels, etc.

The tissue contacting surfaces may also include one or more insulative stop members of any geometric configuration disposed on the inwardly-facing surfaces thereof (in any spatial layout or pattern), which are configured to regulate the gap distance to within the above-mentioned gap range of about 0.001 inches to about 0.006 inches.

The electrode assembly 110, 210 could be selectively detachable (i.e., reposable) from the shaft 12, 212, respectively, depending upon a particular purpose. Alternatively, the entire instrument could be disposable. For example, specific forceps 10, 200 may be configured for different tissue types or thicknesses. Moreover, a reusable forceps 10, 200 could be sold as a kit having different electrodes assemblies 110, 210 and ablative materials for different tissue types. The surgeon simply selects the appropriate electrode assembly and ablative material for a particular tissue type.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An electrode assembly for use with an electrosurgical instrument, the electrode assembly comprising:
    a pair of opposing first and second jaw members being movable relative to one another from a first position wherein the jaw members are disposed in spaced relation relative to one another to a second position wherein the jaw members cooperate to grasp tissue therebetween;
    each jaw member including an electrically conductive tissue contacting surface, each of the tissue contacting surfaces adapted to connect to a source of electrosurgical energy such that the tissue contacting surfaces are capable of conducting electrosurgical energy through tissue held therebetween;
    at least one of the tissue contacting surfaces of one of the jaw members including an energy conductive, ablative material disposed thereon, the energy conductive, ablative material configured to at least partially deplete during electrosurgical activation to reduce tissue adhesion; and
    a sensor adapted to monitor a depletion rate of the energy conductive, ablative material and configured to relay information relating to the depletion rate to the source of electrosurgical energy.

2. An electrode assembly according to claim 1 wherein the energy conductive, ablative material is applied to the at least one of the tissue contacting surfaces prior to electrosurgical application in the form of at least one of a gel and liquid material.

3. An electrode assembly according to claim 1 wherein the energy conductive, ablative material is sterilizeable for a predetermined number of sterilization cycles.

4. An electrode assembly according to claim 1 wherein the energy conductive, ablative material is selected from the group consisting of fiberglass material impregnated with phenolic resin and silica powder, combinations of phenolic resin, polyamide and silica powder; silicone elastomer, rayon-based carbon material and ceramic-forming polymer.

5. A system for sealing tissue, comprising:
    a pair of opposing first and second jaw members being movable relative to one another from a first position wherein the jaw members are disposed in spaced relation relative to one another to a second position wherein the jaw members cooperate to grasp tissue therebetween;
    each jaw member including an electrically conductive tissue contacting surface, at least one of the tissue contacting surfaces adapted to connect to a source of electrosurgical energy such that the tissue contacting surfaces are capable of conducting electrosurgical energy through tissue held therebetween to effect a tissue seal;
    at least one of the tissue contacting surfaces of one of the jaw members including an energy conductive, ablative material disposed thereon, the energy conductive, ablative material configured to at least partially burn off during electrosurgical activation to reduce tissue adhesion;
    a sensor adapted to monitor a depletion rate of the energy conductive, ablative material and configured to relay information relating to the depletion rate to the source of electrosurgical energy; and
    wherein at least one electrical property of the at least one electrically conductive surface is monitored to control energy delivery during electrosurgical activation.

6. An electrode assembly according to claim 5 wherein the at least one electrical property of the electrically conductive surface includes at least one of impedance, current and voltage.

7. An electrode assembly according to claim 5 wherein the energy conductive, ablative material is selected from the group consisting of fiberglass material impregnated with phenolic resin and silica powder, combinations of phenolic resin, polyamide and silica powder; silicone elastomer, rayon-based carbon material and ceramic-forming polymer.

8. The system according to claim 5 further including a source of electrosurgical energy, the source of electrosurgical energy includes at least one of an audible and visual indicator configured to alert a user when the sensor relays information relating to the depletion rate that falls within a predefined threshold.

9. The system according to claim 5 further including a source of electrosurgical energy, the source of electrosurgical energy configured to measure the changes in electrical properties of the at least one tissue contacting surface corresponding to the amount of energy conductive, ablative material depleted over time and modify the electrosurgical energy delivery based thereon to maintain proper energy delivery during electrosurgery.

10. A system for sealing tissue, comprising:
a pair of opposing first and second jaw members being movable relative to one another from a first position wherein the jaw members are disposed in spaced relation relative to one another to a second position wherein the jaw members cooperate to grasp tissue therebetween;
each jaw member including an electrically conductive tissue contacting surface, each of the tissue contacting surfaces adapted to connect to a source of electrosurgical energy such that the tissue contacting surfaces are capable of conducting electrosurgical energy through tissue held therebetween;
at least one of the tissue contacting surfaces of one of the jaw members including an energy conductive, ablative material disposed thereon, the energy conductive, ablative material being configured to at least partially deplete during electrosurgical activation to reduce tissue adhesion;
a sensor adapted to connect to the electrosurgical energy source and configured to relay information relating to a depletion rate to the electrosurgical energy source; and
an indicator configured to alert a user when the relayed information from the sensor relating to the depletion rate falls within a predefined threshold.

11. A system for sealing tissue, comprising:
a pair of opposing first and second jaw members being movable relative to one another from a first position wherein the jaw members are disposed in spaced relation relative to one another to a second position wherein the jaw members cooperate to grasp tissue therebetween;
a source of electrosurgical energy;
each jaw member including an electrically conductive tissue contacting surface, each of the tissue contacting surfaces connected to the source of electrosurgical energy such that the tissue contacting surfaces are capable of conducting electrosurgical energy through tissue held therebetween; and
at least one of the tissue contacting surfaces of one of the jaw members including an energy conductive, ablative material disposed thereon, the energy conductive, ablative material configured to at least partially deplete during electrosurgical activation to reduce tissue adhesion, the energy conductive, ablative material is sterilizeable for a pre-determined number of sterilization cycles,
wherein the source of electrosurgical energy measures the changes in electrical properties of the at least one electrically conductive surface corresponding to the amount of energy conductive, ablative material depleted over time and modifies the electrosurgical energy delivery based thereon to maintain proper energy delivery during electrosurgery.

12. An electrode assembly according to claim 11 further comprising a sensor adapted to connect to the electrosurgical energy source and configured to relay information relating to a depletion rate to the source of electrosurgical energy.

* * * * *